(12) United States Patent
Walz et al.

(10) Patent No.: US 12,318,230 B2
(45) Date of Patent: Jun. 3, 2025

(54) INSTRUMENT WITH HOLDING DEVICE

(71) Applicant: Erbe Elektromedizin GmbH, Tuebingen (DE)

(72) Inventors: Martin Walz, Tuebingen (DE); Fabian Beutler, Neckartenzlingen (DE); Peter Staneker, Engstingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 865 days.

(21) Appl. No.: 17/492,333

(22) Filed: Oct. 1, 2021

(65) Prior Publication Data
US 2022/0104900 A1  Apr. 7, 2022

(30) Foreign Application Priority Data

Oct. 6, 2020 (EP) .................................. 20200293

(51) Int. Cl.
*A61B 50/20* (2016.01)
*A61B 17/00* (2006.01)
*A61M 25/02* (2006.01)

(52) U.S. Cl.
CPC ........ *A61B 50/20* (2016.02); *A61B 17/00234* (2013.01); *A61B 2017/00292* (2013.01); *A61M 2025/028* (2013.01)

(58) Field of Classification Search
CPC ......... A61B 50/20; A61B 2017/00296; A61M 2025/024; A61M 2025/028
See application file for complete search history.

(56) References Cited

U.S. PATENT DOCUMENTS

| 5,309,604 | A | * | 5/1994 | Poulsen | F16L 3/223 24/339 |
|---|---|---|---|---|---|
| 5,364,355 | A | | 11/1994 | Alden et al. | |
| 5,372,592 | A | | 12/1994 | Gambale | |
| 5,830,183 | A | | 11/1998 | Krieger | |
| 5,954,707 | A | * | 9/1999 | Kanesaka | A61M 25/002 604/523 |
| 7,601,150 | B2 | | 10/2009 | Farin | |
| 8,177,736 | B2 | * | 5/2012 | Kopperschmidt | A61M 1/3653 604/4.01 |
| 10,569,055 | B1 | * | 2/2020 | Sigsworth | F16L 3/2235 |
| 2003/0072552 | A1 | | 4/2003 | Wu et al. | |
| 2008/0264993 | A1 | | 10/2008 | Schulte et al. | |
| 2011/0049202 | A1 | | 3/2011 | Besche | |

(Continued)

FOREIGN PATENT DOCUMENTS

| CN | 102448388 A | 5/2012 |
|---|---|---|
| CN | 102596063 A | 7/2012 |

(Continued)

*Primary Examiner* — James R Bidwell
(74) *Attorney, Agent, or Firm* — Blank Rome LLP

(57) ABSTRACT

An endoscopic instrument having an instrument body configured in a long, slim and flexible manner. The instrument may be completely or partly wound in one or more windings that allows the instrument to be packed in a space-saving and easy-to-handle manner. To keep the instrument body in this position, a holding device is provided that is arranged on the instrument body and is preferably undetachably held there. The holding device has a gripper rotatably supported around the instrument body. The instrument body has a latch to hold and fasten the windings.

15 Claims, 8 Drawing Sheets

(56) References Cited

U.S. PATENT DOCUMENTS

| | | |
|---|---|---|
| 2012/0220897 A1 | 8/2012 | Taylor |
| 2014/0259544 A1 | 9/2014 | Sigmon, Jr. |
| 2016/0074628 A1* | 3/2016 | Smith .................. A61B 1/0014 604/174 |
| 2019/0346643 A1* | 11/2019 | Chu ..................... G02B 6/4439 |

FOREIGN PATENT DOCUMENTS

| | | |
|---|---|---|
| CN | 111093547 A | 5/2020 |
| DE | 102016211654 A1 | 12/2017 |
| EP | 0 888 793 A1 | 1/1999 |
| GB | 9212557 | 7/1992 |
| SU | 1736450 A1 | 5/1992 |
| WO | WO 03/000150 A1 | 1/2003 |
| WO | WO 2010/068739 A1 | 6/2010 |

\* cited by examiner

INSTRUMENT WITH HOLDING DEVICE

CROSS-REFERENCE TO RELATED APPLICATION

This application claims priority to European Application No. 20200293.7, filed Oct. 6, 2020, the entirety of which is incorporated by reference herein.

TECHNICAL FIELD

Embodiments of the invention refer to an instrument for treatment of human and animal patients, particularly an instrument for endoscopic treatment.

BACKGROUND

Probes for surgical treatment of a patient for endoscopic use are generally known from the prior art. For example, WO 03/00150 A1 discloses a probe for argon plasma coagulation. The instrument comprises a long instrument body with at least one flexible section. The flexible section is suitable for insertion into a working channel of the endoscope.

During use of the instrument on a patient it can happen that the instrument has to be pulled out of the working channel of the endoscope and temporarily laid down, e.g. in a respective aseptic bowl, in order to temporarily insert another instrument in the working channel of the endoscope, for example. During temporary storage of the instrument in an aseptic bowl or at another suitable location, the instrument generally cannot come into contact with other objects in a non-controlled manner, e.g. non-sterile objects or surfaces. Due to the length of the instrument that can, for example, exceed two meters, this cannot be readily guaranteed by default. For example, it can be expedient to pack the instrument in several windings. Due to the typically inherent spring elasticity thereof, it has however the tendency to spring back in a stretched form. It is known from U.S. Pat. No. 5,372,592 A as well as WO 2010/068739 A1 to attach the packed instrument by means of a clamp. The clamp can be configured in the type of a helical spring according to US 2012/0220897 A1 that comprises a spirally expanding winding on one end. However, the handling is troublesome and is a hygienic risk. U.S. Pat. No. 5,364,355 proposes to arrange a sleeve having a helical groove in a longitudinally movable and rotatable manner on a proximal section of the flexible instrument. EP 0 888 793 A1 proposes to arrange a clamp with a movable bracket on the proximal end of the instrument that is pivotable between an open position and a closed position back and forth. On the contrary, US 2014/0259544 A1, US 2008/0264993 A1 and WO 2010/068739 A1 use rigid clamps arranged immovably on the instrument for holding windings of a packed instrument. For holding a light conductor, US 2003/0072552 A1 proposes a holder that comprises an end having two mounting holes and a section adjoining thereto having a sheet metal strip bent to form a spiral. The light conductor can be inserted therein.

SUMMARY

It is the object of embodiments of the invention to provide an improved concept for handling the instrument, particularly during non-use thereof.

This object is solved by means of an instrument according to claim 1 and by means of a holding device according to claim 15:

An embodiment of the inventive instrument is particularly provided for endoscopic use. For example, the instrument is a probe that can be inserted in a working channel of an endoscope and can be moved in different directions by means of the end of the endoscope that can be angled. For this purpose the instrument comprises an instrument body having at least one flexible section. The flexible section can have a length of more than 1 meter, for example, and can be wound in at least one and preferably multiple windings. A holding device arranged on the instrument body is part of the instrument, wherein the holding device can hold and fasten one or more winding(s). The instrument body can be formed by a hose having one or more lumen with a cylindrical outer contour, i.e. a circular cross-section. The instrument body can also have a non-circular, e.g. oval, cross-section or can consist of two or more hoses arranged parallel to one another.

Due to the arrangement of the holding device on the instrument body, the holding device can be operated with one hand, namely the hand that holds the instrument body. By means of the claimed configuration of the holding device, it has a short axial dimension and is thus easy to handle. With the other hand the operating person can pack the instrument body in one or more windings and can operate the holding device with one of his/her hands in order to arrange and fasten the windings. With this concept a simple handling is achieved and dangers for the sterility of the instruments are eliminated. The holding device arranged on the instrument body is as aseptic as the instrument body itself. Since having the holding device is non-releasably connected with the instrument body, it cannot be laid down aside thereof. The danger of contamination is minimized.

By means of embodiments of the invention the temporary storage of the instrument during an instrument change is simplified. The instrument can be packed with low required space and fastened quickly and in a simple manner. Instruments with a length of more than 2 meters can be safely handled in this manner, while avoiding that the packed windings spring open and, for example, fall to the ground.

The instrument body can consist of a supply section and a probe section. The probe section and the supply section can have different diameters, can consist of different materials and/or can have different flexibilities. The instrument body can, however, also be formed continuously by a hose of uniform thickness and/or of one and the same material. However, also in this case the part of the instrument body that is to be inserted in an endoscope can be considered as probe section. The part of the instrument body that remains outside the endoscope during a treatment can be considered as supply section. The holding device is preferably arranged on the supply section. It can be held there in an axially non-movable manner, i.e. it can be secured against axial displacement. Alternatively, the holding device can also be arranged on the probe body axially displaceable in a limited manner. For example, the axial movement range can be limited on both sides by means of stop elements. A stop element can be formed on one side by the handle of the instrument. Further, a stop element can be formed by a rubber element, e.g. an O-ring, on one side or on both sides.

For example, the instrument can be an argon plasma probe that comprises a channel extending from the proximal end to the distal end that can be supplied with gas and an electrode arranged therein. However, the instrument can also be another instrument, e.g. an instrument for cryotreatment, a fiber optical instrument for laser treatment or the like. However, it is common for all these instruments that they comprise a slim long instrument body that is flexible, at least in sections, such that it can be packed to form one or more windings.

Preferably the holding device comprises a gripper that is rotatably supported relative to the instrument body. The gripper is preferably a one-piece rigid plastic part without movable sections. The rotation axis of the gripper is thereby preferably identical to the longitudinal direction of the instrument body or parallel thereto. This allows a particular simple ergonomic handling by the user. With the hand in which he or she holds the instrument body, he or she can concurrently rotate the rigid gripper of the holding device. The gripper can thereby take up and fasten one or more windings of the packed instrument body that is possibly held with the other hand of the user.

For this purpose it is particularly advantageous, if the gripper comprises a holding space for the probe section, wherein the holding space is curved around the instrument body, particularly around the longitudinal axis thereof. Thus, the gripper is hook-like formed with viewing direction parallel to the longitudinal direction of the probe body. Thereby the holding space is preferably longer along an arc-shaped path curved around the rotation axis of the gripper than one third of the circumference of the gripper, particularly preferably longer than the half circumference of the gripper. In doing so, multiple windings of the instrument body can be reliably grasped and held.

One or more structures for holding a section of the instrument body, particularly its distal end section, can be provided on the holding device. These structures can serve to fasten the distal end of the instrument body such that it remains with the compactly packed instrument body. Thereby it is particularly achieved to protect the distal end of the instrument body from contamination and thus the patient from getting into contact with germs or dirt.

Structures for at least temporary holding and disposal of the distal end of the instrument body can be one or more latch recesses that are arranged on a base of the holding device or on the rotatably supported gripper. Such latch recesses can be C-shaped recesses in which the probe hose can be clipped. The configuration of such latch recesses in the gripper has the particular advantage that as soon as the distal end or another section of the instrument body has clipped in the latch recess, also the further rotation of the gripper is blocked and the windings of the instrument are secured in the gripper. The end of the instrument held in the latch recess blocks the path out of the gripper for the windings.

BRIEF DESCRIPTION OF THE DRAWINGS

Further details of advantageous embodiments and modifications of the invention are subject of the claims as well as the figures of the drawings and the respective description. The drawings show:

DETAILED DESCRIPTION

Figure 1:
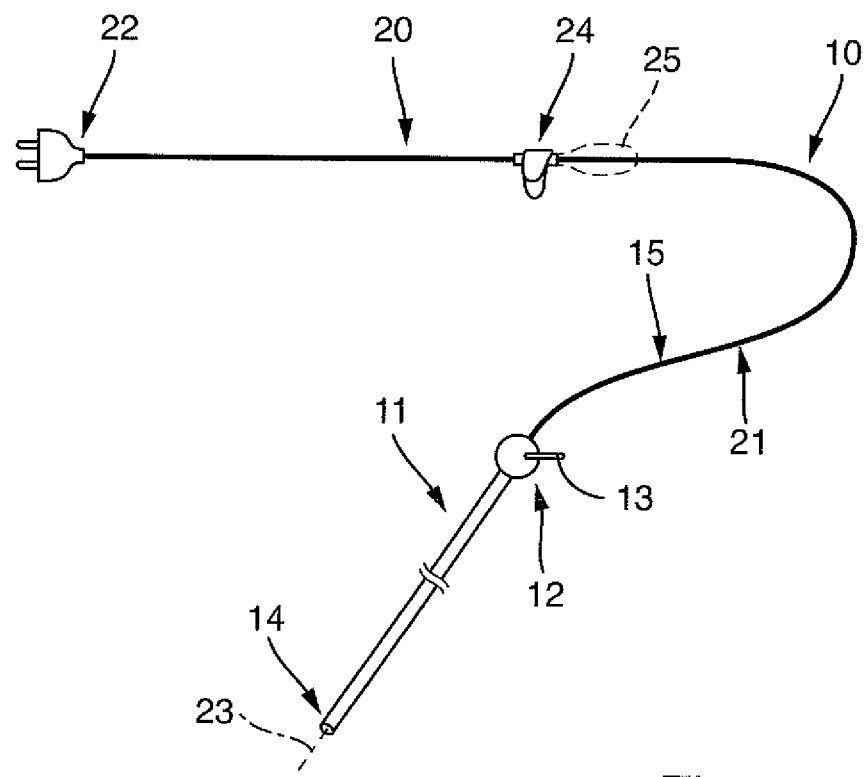
FIG. 1 an endoscope with an instrument inserted therein in a schematic total illustration, FIG. 2 the packed instrument taken out of the endoscope in a total illustration, FIG. 3 the instrument cut at the holding device at a cross-sectional view, FIG. 4 the holding device in a perspective explosion illustration, FIG. 5 the instrument and the holding device in a partly longitudinal sectional illustration, FIG. 6 a base that is part of the holding device in a front view, FIG. 7 a gripper that is part of the holding device in a perspective illustration, FIG. 8 the gripper of FIG. 7 in a different perspective illustration, FIG. 9 a modified embodiment of the holding device for an instrument having a double hose arrangement in the supply section, FIG. 10 an instrument having two hoses in the supply section and a holding device having a base, and FIG. 11 an instrument having a holding device without base in a cross-sectional illustration cut in the vicinity of its holding device.

An instrument 10 is illustrated in FIG. 1 that is configured as flexible probe and is provided for use in an endoscope 11. The endoscope 11 comprises a working channel that extends through the instrument 10. In addition, the endoscope 11 comprises an operating unit 13 at its proximal end 12 that serves to control the distal end 14 of the endoscope, e.g. to angle it laterally.

The instrument 10 can be any instrument appropriate for treatment of a human or animal patient. It can particularly be a cryosurgical instrument, an electrosurgical instrument, a plasmasurgical instrument or also an instrument for treatment with radio waves or light, e.g. a fiber optic instrument for laser treatment of biological tissue. In the context of embodiments of the present invention it is important that the instrument 10 comprises an instrument body 15 having a flexible section 16 that can be packed in one or more windings 17, 18, 19, as illustrated in FIG. 2.

For example, the instrument body 15 can be formed by a supply section 20 and a probe section 21. Both sections 20, 21 can consist, for example, of a hose having one or multiple lumen. The material of the supply section 20 can be the same material as the material of the probe section 21. However, also different materials can be used. However preferably, the supply section 20 as well as the probe section 21 consists of plastic. The supply section 20 and the probe section 21 can have a round cross-section and can comprise equal or different diameters. Likewise the supply section 20 and the probe section 21 can comprise equal or different flexibilities. It is also possible to form the supply section 20 by a single continuously formed body.

At the proximal end of the instrument 10 connection means, e.g. a plug 22, can be provided, via which the instrument 10 can be supplied with current and/or operating media, light or other forms of energy. The distal end 23, however, serves to influence biological tissue on or in the patient.

Figure 2:
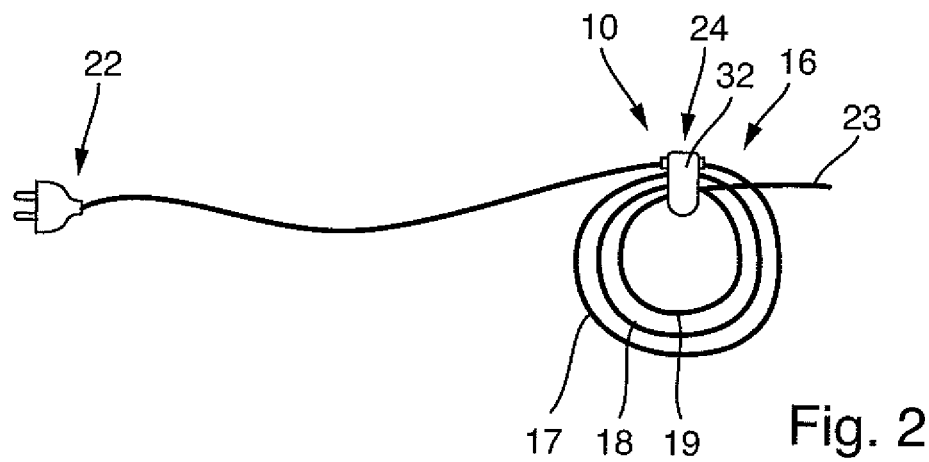

According to embodiments of the invention, the instrument 10 comprises a holding device 24 that serves to hold the windings 17, 18, 19 of the instrument 10 together, as illustrated in FIG. 2. As illustrated in FIG. 1, the holding device 24 can, for example, be arranged in the proximity of a handle 25 that is optionally provided and therefore illustrated in dashed lines in FIG. 1. It serves to handle the instrument 10, particularly during insertion in the endoscope 11 and/or during the treatment of the patient. For example, the handle 25 can be arranged at a location of the instrument 10 at which the supply section 20 adjoins the probe section 21.

Figure 3:
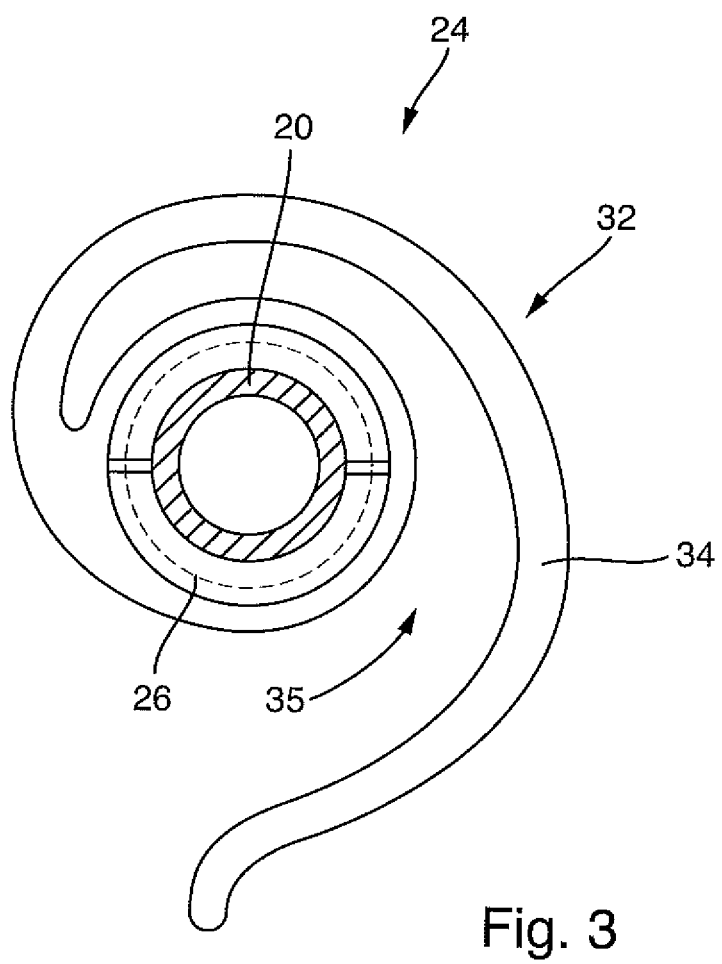
Figure 4:
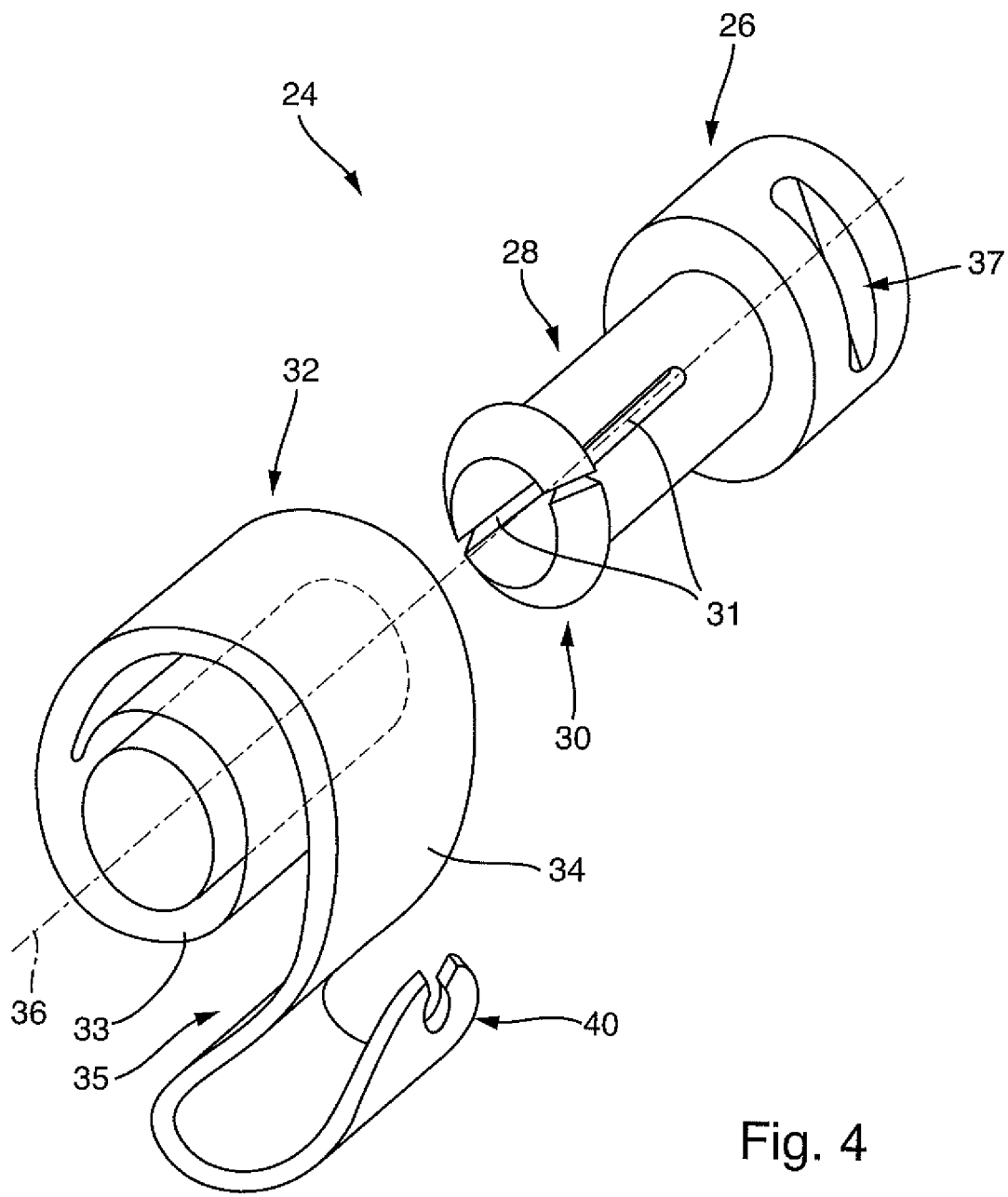
Figure 5:
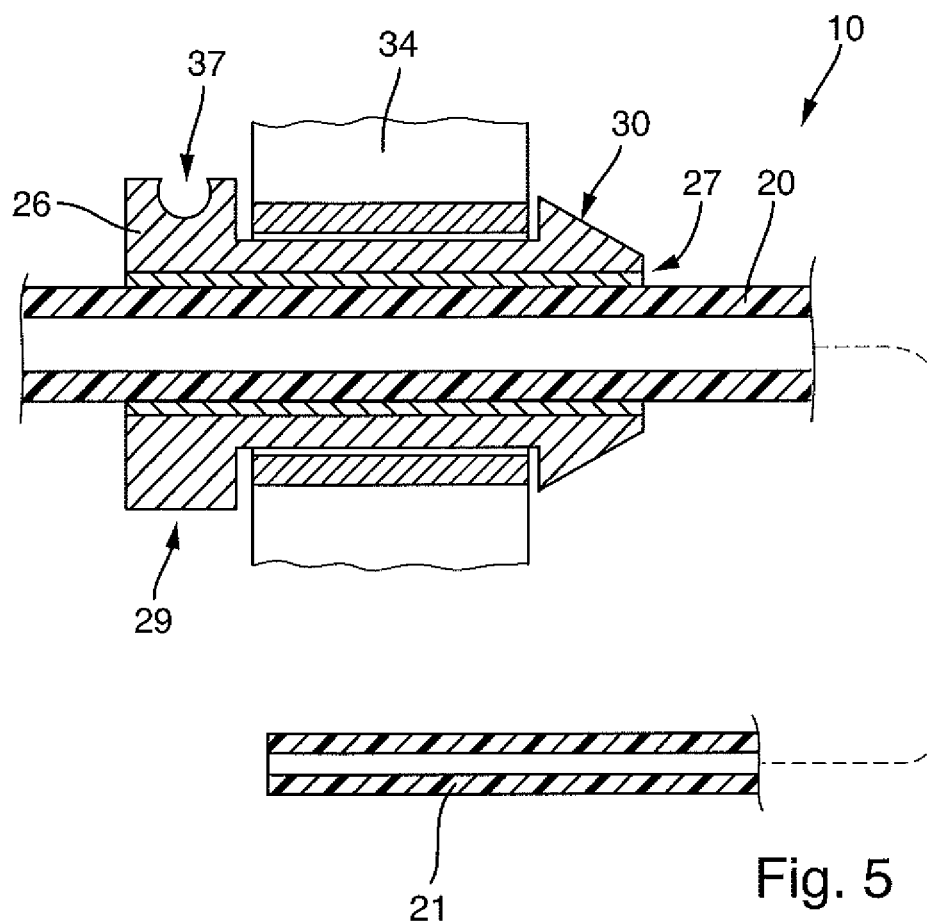

The holding device 24, preferably arranged on the supply section 20, is illustrated in FIGS. 3, 4 and 5. The holding device 24 can comprise a base 26, preferably made of plastic that is arranged on the instrument 10, e.g. on the supply section 20. The base 26 can be arranged on the instrument 10, e.g. on the supply section 20, as suggested in FIG. 5. Thereby the base 26 can be clamped or glued or secured in another manner against axial displacement on the supply section 20. Only by way of example an adhesive layer 27 is illustrated for this purpose in FIG. 5. As an alternative, the base 26 can be held on the outer surface of the instrument 10 in a friction-fit manner, e.g. by means of rubber elements, e.g. rubber rings. It is also possible to arrange the base 26 axially displaceable with play on the instrument 10, particularly the supply section 20. The base 26 can, however, also be omitted.

Preferably the base 26 comprises a support section 28 that is cylindrical on the outer side and adjoined by a radially outwardly projecting head 29. On the other end of the support section 28 a latch collar 30 is provided, having a ring surface that limits the support section 28 axially. Longitudinal slits 31 that can extend into the support section 28 separate the latch collar 30 such that its halves are able to flex radially inwardly.

Independent from whether the holding device 24 comprises a base 26 or not, a gripper 32 is part of the holding device 24 that is rotatably held at the instrument 10. For example, the gripper can be held on the support section 28. Alternatively, the gripper 32 can also be directly rotatably held on the instrument 10. The gripper 32 is preferably a plastic part. It comprises, for example, a tube-shaped center part 33 from which a hook-shaped or helically shaped latch 34 extends away. The center part 33 can be configured like a sleeve with closed wall. Alternatively, the center part 33 can comprise a longitudinal slit to be attached to the instrument 10 or the base 26 by means of a clip-on movement.

The latch 34 thereby winds around the center part 33 with distance thereto. In this manner the latch 34 together with the tube-shaped center part 33 limits the curved holding space 35, the width (i.e. the distance toward the center part 33) and the depth of which are sufficient to hold the windings 17, 18, 19, e.g. of the probe section 21. The holding space 35 extends in an arc-shaped manner around the tube-shaped center part 33 and thereby extends preferably about more than a half turn, i.e. more than 180° around the center axis 36.

Figure 6:
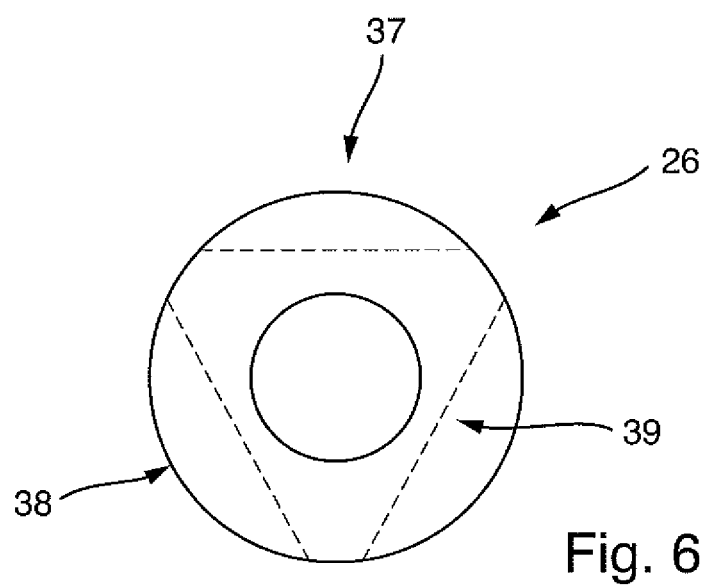
Figure 7:
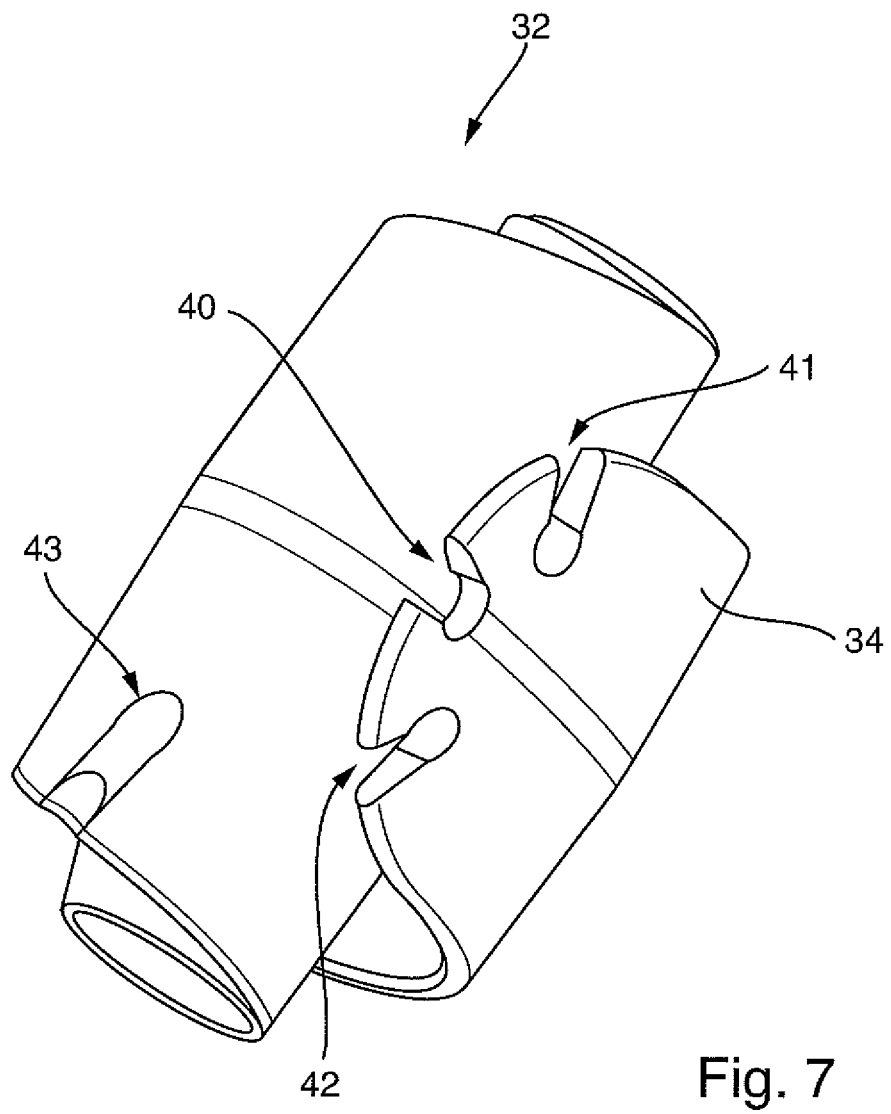
Figure 8:
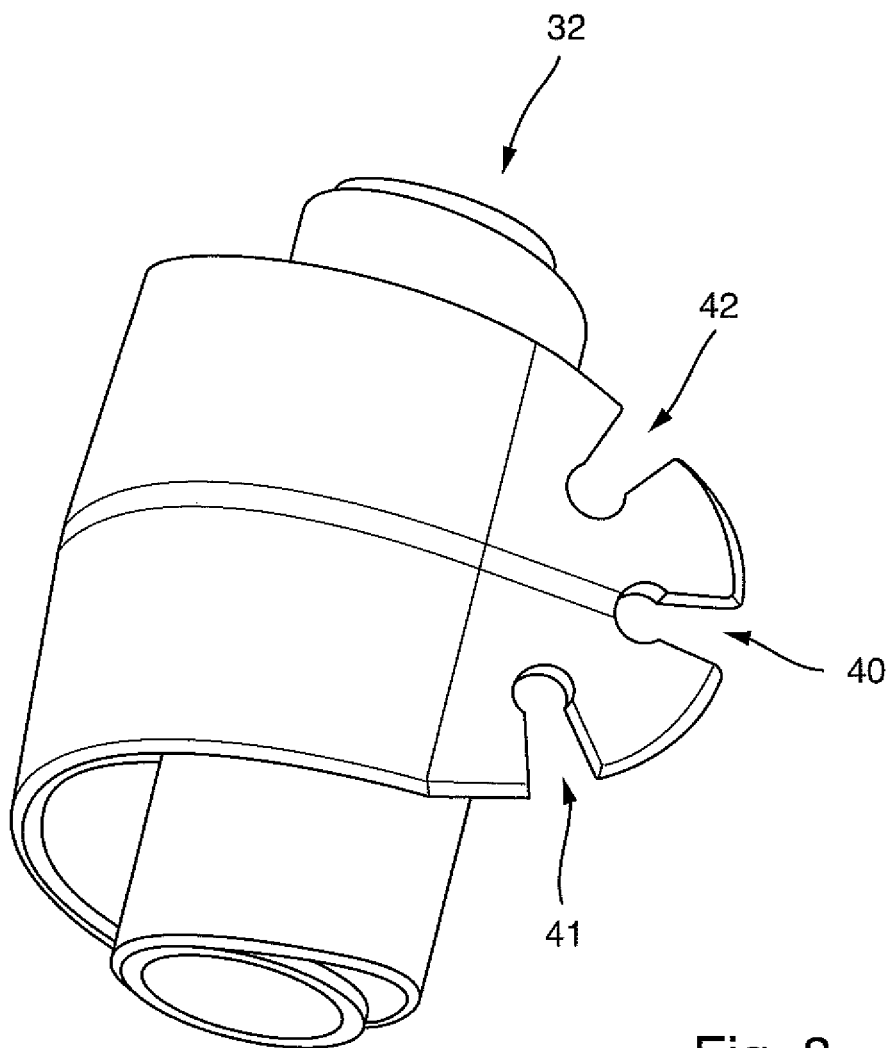

One or more latch recesses 37, 38, 39 can be configured on the base 26, as particularly apparent from FIGS. 4, 5 and 6. Preferably the latch recesses 37-39 are formed in the head 29 of the base 26, e.g. in the form of straight grooves that are in the center region slightly narrower than the diameter of the probe section 21. The distal end 23 or the part of the probe section 21 adjoining in proximal direction can thus be clipped in the latch recesses 37-39 and is in this manner temporarily attached. It is, however, also possible to form a latch recess 40 on the free end of the latch 34, as apparent from FIG. 4. The distal end 23 of the probe section 21 or an adjoining part thereof can be inserted in this latch recess 40. It is also possible to form multiple of such latch recesses 40, 41, 42 on the free end of the latch 34 of the gripper 32. Likewise a further latch recess 43 can be arranged in the flank of the latch 34. Such latch recesses 40-42 are also apparent from FIG. 8.

The instrument 10 described so far can be provided and delivered by an instrument manufacturer aseptically packed, e.g. in a packed form illustrated in FIG. 2, the windings 17, 18, 19 can be released by rotation of the gripper 32, such that the instrument 10 can be connected with a supplying apparatus on one hand and can be inserted in the working channel of an endoscope 11 on the other hand.

If the instrument 10 has to be removed from the working channel of the endoscope 11 during a surgery and set aside intermediately, it can be simply packed again, as illustrated in FIG. 2, in that particularly its probe section 21 is wound in several windings 17, 18, 19. This is readily possible with two hands, wherein the gripper 32 can be rotated with one hand such that it holds and secures the windings 17, 18, 19. If required, now the distal end 23 can be additionally secured in one of the latch recesses 37-43. If the latch recesses 40, 41, 42 or also the latch recess 43 is used, a turn back of the gripper 32 can be blocked thereby. This is an additional security against unfolding of the windings 17, 18, 19. The instrument 10 reliably packed in this manner can now be intermediately stored, for example in an aseptic bowl, without the danger of uncontrolled movements and contamination.

Figure 9:
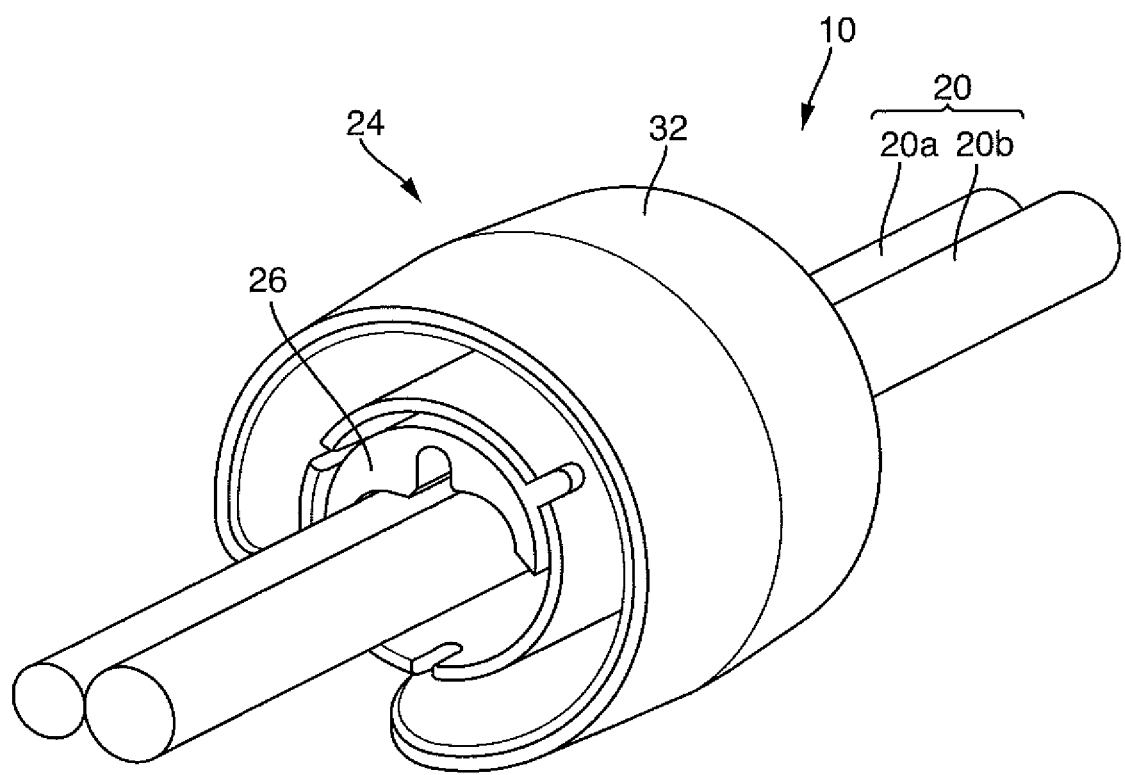
Figure 10:
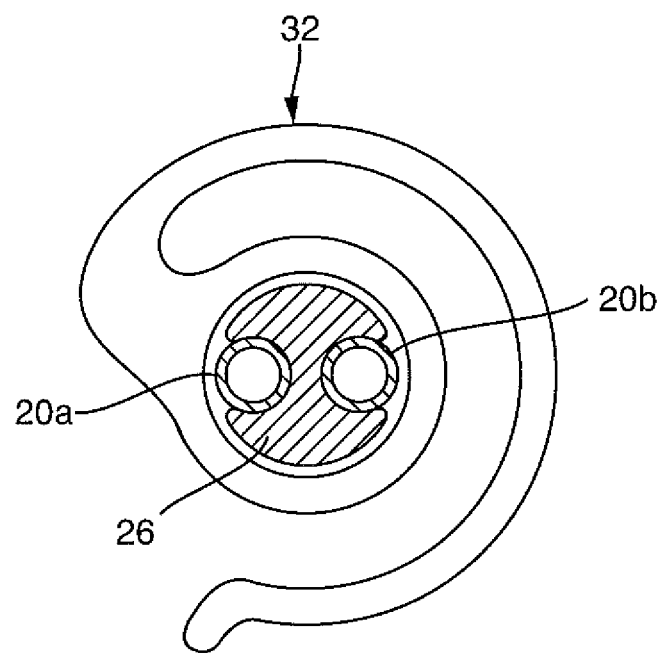

An instrument 10 is further apparent from FIG. 9 that comprises two lines 20a, 20b in its supply section 20. The base 26 is configured for arrangement of both lines 20a, 20b. However, it has not necessarily to surround these along the complete circumference, wherein a slimmer configuration can be achieved. A similar configuration is apparent from FIG. 10. There, also, a base 26 is provided for arrangement of both lines 20a, 20b that can be glued to the two lines 20a, 20b, as in the embodiment according to FIG. 9 or can be in a clip-on connection therewith. With regard to the embodiment of the gripper 32, the descriptions provided to all other embodiments apply accordingly.

Figure 11:
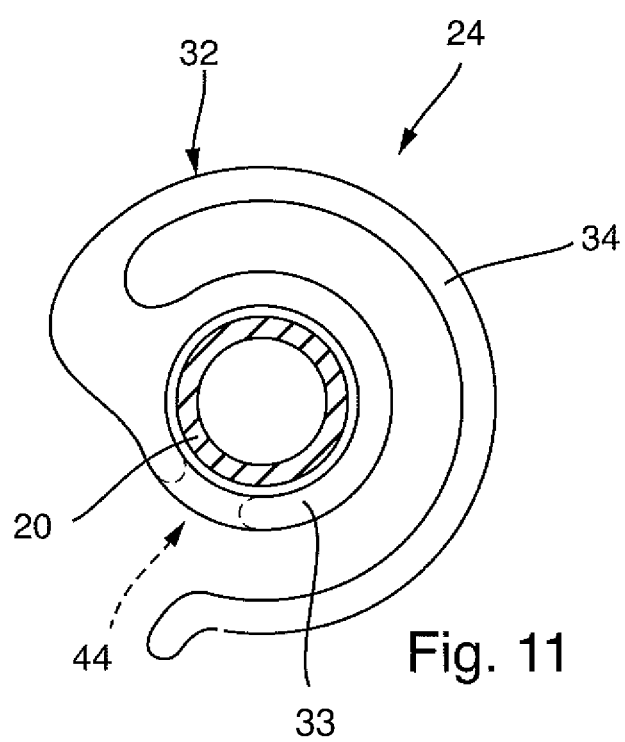

An embodiment of the holding device 24 is apparent from FIG. 11 in which the gripper 32 is held without base directly on the supply section 20 or also on another section of the instrument 10. It is thereby rotatable about the longitudinal axis of the supply section 20, i.e. it is held with some radial play on the supply section 20. In addition, the gripper 32 is axially movable on the supply section 20. For limiting the movement path respective stop elements can be provided that are not illustrated. Stop elements can be, e.g. O-rings attached on the supply section 20, structures formed by clip element or also structures naturally provided on the instrument, such as the handle. The tube-shaped center part 33 can be configured as closed hollow cylinder like a sleeve, as illustrated in FIG. 11. As an alternative, it is also possible to form a slit 44 in the central section 32, if appropriate with rounded flanks, as illustrated in FIG. 11 by dashed lines. This has the advantage that the gripper 32 can then be clipped on the respective support structure, i.e. a base or also the supply section 20 or another part of the instrument 10. In doing so, the gripper 32 is also suitable for subsequent attachment on an instrument 10 that previously was not equipped with a holding device 24. The slit 44 can be used in all of the above-described embodiments.

Each of the above described are in context with the instrument 10 subsequently claimed holding devices 24 can also be provided and marketed independent from the instrument 10. In such cases the holding device 24 has to be subsequently attached to the instrument 10.

Embodiments of the inventive instrument 10 comprise an instrument body 15 that is particularly configured in a long slim and flexible manner. It can be completely or partly wound in at least one or multiple windings 17, 18, 19 and can in this way be packed in a space-saving and easy-to-handle manner. In order to keep the instrument body 15 in this position, a holding device 24 is provided that is arranged on the instrument body 15 and is preferably undetachably held there. The holding device comprises a gripper 32 rotatably supported around the instrument body having a latch 34 that is able to hold and fasten the windings 17, 18, 19. The gripper 32 can be handled with the fingers of the hand with which the user holds the instrument 10.

The invention claimed is:

1. An endoscopic instrument comprising:
   an instrument body that comprises at least one flexible section that can be wound in at least one winding; and
   a holding device that comprises a gripper for holding the at least one winding that is rotatably supported on the instrument body, the gripper comprising,
      a tube-shaped center part and a latch extending away from and fixedly attached to the tube-shaped center part, the latch having a radial distance around at least a part of the circumference of the tube-shaped center part and defining a curved holding space that is configured to remain open, wherein the holding space extends more than a half turn around a center axis of the center part.

2. The endoscopic instrument of claim 1, wherein the instrument body further comprises a supply section and a probe section.

3. The endoscopic instrument of claim 2, wherein the probe section is flexible and can be wound in at least one winding.

4. The endoscopic instrument of claim 1, wherein the gripper is a one-piece rigid plastic part.

5. The endoscopic instrument of claim 4, wherein the gripper is arranged on a base and rotatably supported.

6. The endoscopic instrument of claim 4, wherein the holding space is configured to receive a probe section, and wherein the holding space is curved around the instrument body.

7. The endoscopic instrument of claim 6, wherein the holding space is longer than one third rotation of the gripper in rotation direction of the gripper.

8. The endoscopic instrument of claim 4, wherein the gripper comprises at least one latch recess for holding a section of the instrument body.

9. The endoscopic instrument of claim 5, wherein the base comprises at least one latch recess for holding a section of the instrument body.

10. The endoscopic instrument of claim 1, wherein the holding device is secured on the instrument body in a non-displaceable manner.

11. The endoscopic instrument of claim 1, wherein the holding device is undetachably held on the instrument body.

12. The endoscopic instrument of claim 2, wherein the holding device comprises a base configured for attachment to an instrument having a non-round cross-section.

13. The endoscopic instrument of claim 12, wherein the base surrounds the supply section or the probe section around the whole circumference or alternatively, only around a part of its circumference.

14. The endoscopic instrument of claim 2, wherein the holding device is axially movably arranged on the supply section or the probe section.

15. An endoscopic instrument, the endoscopic instrument comprising:
   an instrument body having at least one flexible section configured to be wound in at least one winding;
   a holding device having;
      a base,
      a gripper rotatably arranged on the instrument body, and
      a tube-shaped center part from which a latch extends away in radial distance to the center part around at least a part of the circumference of the center part to define a holding space that extends more than a half turn around a center axis of the center part.

* * * * *